United States Patent
Wu et al.

(10) Patent No.: US 7,196,794 B2
(45) Date of Patent: Mar. 27, 2007

(54) SYSTEMS AND METHODS FOR LIMITING POWER USING PHOTO-INDUCED ANISOTROPY

(75) Inventors: Pengfei Wu, Malden, MA (US); Reji Philip, Bangalore (IN); Devulapalli V. G. L. N. Rao, Lexington, MA (US)

(73) Assignee: University of Massachusetts, Boston, MA (US)

( * ) Notice: Subject to any disclaimer, the term of this patent is extended or adjusted under 35 U.S.C. 154(b) by 48 days.

(21) Appl. No.: 10/877,777

(22) Filed: Jun. 25, 2004

(65) Prior Publication Data

US 2005/0135454 A1    Jun. 23, 2005

Related U.S. Application Data

(60) Provisional application No. 60/483,831, filed on Jun. 30, 2003.

(51) Int. Cl.
*G01J 4/00* (2006.01)
(52) U.S. Cl. ..................... 356/370; 356/364
(58) Field of Classification Search ............ 356/364, 356/365, 367, 368, 369, 370; 250/559.09, 250/225
See application file for complete search history.

(56) References Cited

U.S. PATENT DOCUMENTS 6,606,181 B2 * 8/2003 Patel et al. ................ 359/238

OTHER PUBLICATIONS

Wu et al., "Optical Power Limiting With Photoinduced Anisotropy Of Azobenzene Films," Applied Optics, vol. 42, No. 22, Aug. 1, 2003.

Frey et al., "Optical Limitation In Resonant Faraday Media," Optical Letters, vol. 25, No. 11, Jun. 1, 2000.

Dovgalenko et al., "Optically Induced Birefringence In Bacteriorhodopsin As An Optical Limiter," Appl. Phys. Lett. 68 (3), Jan. 15, 1996.

* cited by examiner

*Primary Examiner*—Gregory J. Toatley, Jr.
*Assistant Examiner*—Roy M. Punnoose
(74) *Attorney, Agent, or Firm*—Weingarten, Schurgin, Gagnebin & Lebovici LLP (57) ABSTRACT

Preferred embodiments of the present invention are directed at limiting power and controlling an output intensity of an optical system using photo-induced anisotropic materials. In a preferred embodiment, an azobenzene polymer film is used. The embodiments in accordance with the present invention include a cross-polarization system to provide clamping of the output intensity.

A system for limiting power in accordance with a preferred embodiment of the present invention, includes a light source that provides an input light beam along a first optical path, a first polarizing element having a first polarization state positioned in the first optical path, a second polarizing element positioned in the first optical path having a second polarization state substantially orthogonal to the first polarization state, a sample having a photo-induced anisotropic material positioned in the first optical path, and a polarizer positioned in a second optical path at an angle of approximately 45 degrees to that of the input beam wherein an excitation beam provided in the second optical path spatially overlaps the input beam on the sample, and an output beam that is generated has a limited transmission value at high intensity.

20 Claims, 9 Drawing Sheets

SYSTEMS AND METHODS FOR LIMITING POWER USING PHOTO-INDUCED ANISOTROPY

CROSS REFERENCES TO RELATED APPLICATIONS

The present application claims the benefit of U.S. Provisional Application No. 60/483,831, filed Jun. 30, 2003. The entire contents of the above applications are incorporated herein by reference in entirety.

GOVERNMENT SUPPORT

This invention was supported, in whole or in part, by a Broad Agency Announcement contract DAAD 16-01-C-0018 from the U.S. Army Natick Research Laboratory. The Government has certain rights in the invention.

BACKGROUND OF THE INVENTION

The rapid development of laser technology has made portable laser systems with high power and energy available. The lasers are widely used for many applications and have greatly advanced scientific research. As they are used everywhere, the odds of a laser beam accidentally hitting a person are increasing. Even low-power lasers can damage human eyes or photosensors. As such, studies of optical power limiting and design of devices are receiving lot of interest. Several optical techniques with various materials including inorganic, organic and biological molecules have been used for such applications. Nonlinear absorption effects such as reverse saturable absorption including excited state absorption and multi-photon absorption have been widely studied with high power pulsed lasers for limiting power. Light scattering is also used to limit the optical power when a strong beam is incident on some materials and it can enhance the nonlinear absorption. Another important nonlinear optical effect used for limiting power is beam diffusing, which originates from the change of spatial distribution of the refractive index and manifests as self-defocusing, beam fanning (diffusive photovoltaic thermal effects), and the Kerr effect. The filtering features associated with the holographic technique and photonic bandgap materials are also useful for power-limiting applications.

Recently, polarization rotation in resonant Faraday media sandwiched between crossed polarizers and bacteriorhodopsin materials placed between a pair of parallel polarizers has been studied theoretically and experimentally and can be used for optical limiting applications. These polarization rotation techniques may offer many advantages such as, for example, low-fluence threshold, high-intensity range, and ease of improvement with new materials for practical applications, particularly for protecting human eyes and sensitive optical sensors that can be damaged by even low-power laser beams. However, all these systems have been only demonstrated in the laboratory with high power laser systems and are far from practical in different applications. There remains a need for systems and methods to limit the power in optical systems.

SUMMARY OF THE INVENTION

Preferred embodiments of the present invention are directed at limiting power and controlling an output intensity of an optical system using photo-induced anisotropic materials. In a preferred embodiment, an azobenzene polymer film is used. The embodiments in accordance with the present invention include a cross-polarization system to provide clamping of the output intensity.

A system for limiting power in accordance with a preferred embodiment of the present invention, includes a light source that provides an input light beam along a first optical path, a first polarizing element having a first polarization state positioned in the first optical path, a second polarizing element positioned in the first optical path having a second polarization state substantially orthogonal to the first polarization state, a sample having a photo-induced anisotropic material positioned in the first optical path, and a polarizer positioned in a second optical path at an angle of approximately 45 degrees (i.e. in a range of 35–55 degrees) to that of the input beam wherein an excitation beam provided in the second optical path spatially overlaps the input beam on the sample, and an output beam that is generated has a limited transmission value at high intensity.

In a preferred embodiment of the optical power limiter system the light source is a continuous wave laser or a pulsed laser. The sample comprises an azobenzene material embedded in a polymer. The polymer is one of polystyrene, polycarbonate or a matrix of polymethylmethacrylate (PMMA). In a preferred embodiment, the sample is integral with an eye protection goggle. The wavelength of the input beam is in a range between near infra-red radiation and the visible spectrum. The system in accordance with a preferred embodiment of the present invention further includes a detector system such as, a power meter. The system can include an incoherent light source to generate the excitation beam such as, for example, a laser diode or light emitting diode.

In accordance with another aspect of the present invention, a method of limiting optical power, includes the steps of generating an input beam from a first light source, generating a linearly polarized excitation beam, exposing a sample having a photo-induced anisotropic material to the input beam and the excitation beam; and clamping the transmission of an output beam by cross-polarizing the input.

In accordance with another aspect of the present invention, an eye protection device, includes a light source to provide an input light beam along a first optical path, a first polarizing element having a first polarization state positioned in the first optical path, a second polarizing element positioned in the first optical path having a second polarization state substantially orthogonal to the first polarization state, a sample having a photo-induced anisotropic material positioned in the first optical path; and a polarizer positioned in a second optical path at an angle of approximately 45 degrees to that of the input beam wherein an excitation beam provided in the second optical path spatially overlaps the input beam on the sample, and an output beam that is generated has a limited transmission value at high intensity.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The preferred embodiments of the present invention are directed at limiting power and in particular with photo-induced anisotropic effects of azobenzene polymer films. Power limiting can be achieved in selective regions such as, for example, the low power region (milliwatts) and high power region. The results obtained using preferred embodiments including a crossed polarizer arrangement illustrate clamping close to that of an ideal optical limiter. In addition, the use of crossed polarizers in the embodiments offer an unmistakable advantage in terms of safety. In two worse case situations, where either the excitation beam gets accidentally blocked or the film becomes transparent by photo-damage, the device in accordance with a preferred embodiment remains within safe limits by virtue of the presence of the crossed polarizers. The results of the preferred embodiment are also demonstrated to be useful for many photonics applications including optical switches, spatial light modulators, and medical image processing.

Figure 1A:
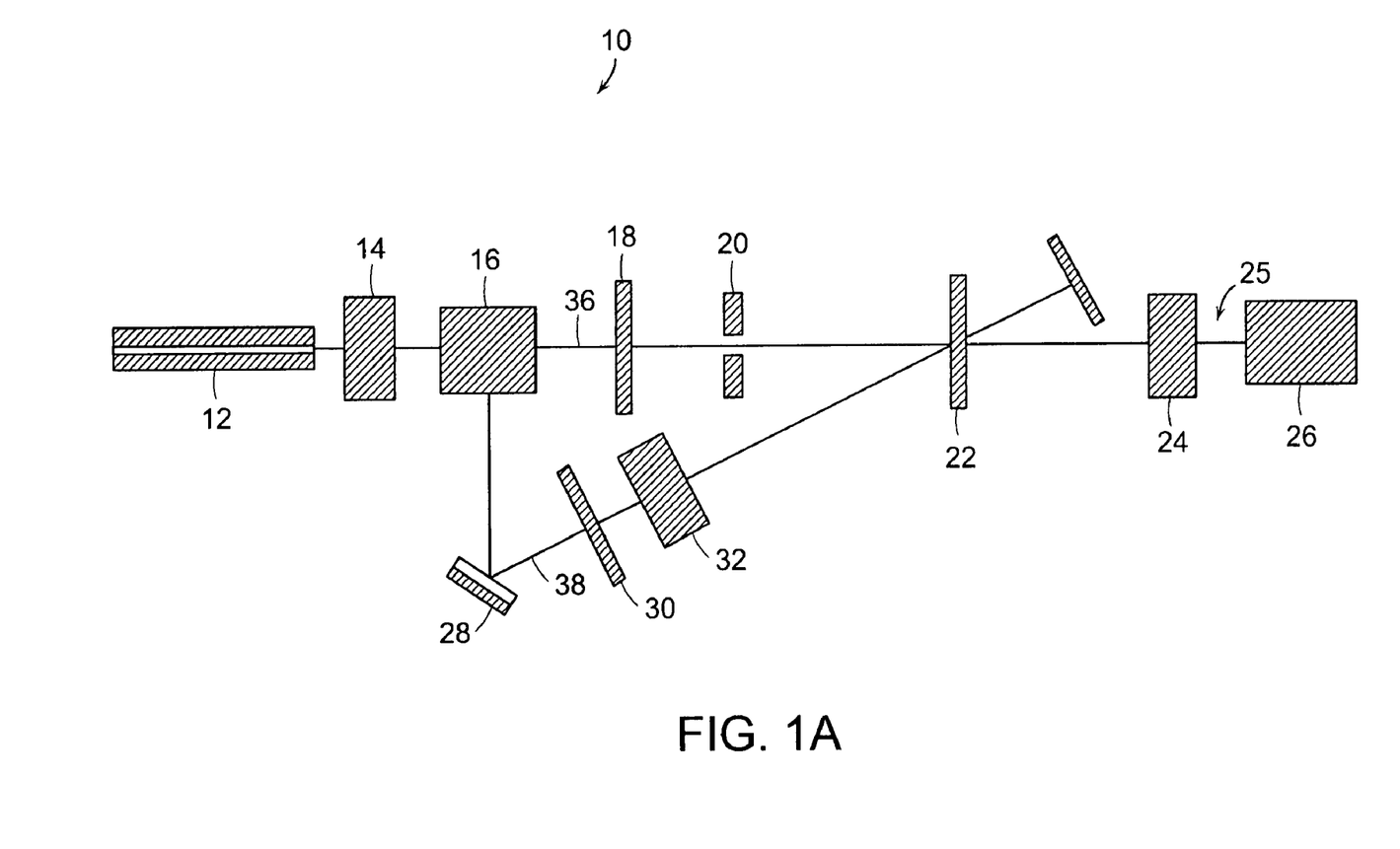
FIG. 1A illustrates a schematic of a system in accordance with a preferred embodiment of the present invention for optical power limiting using photo-induced anisotropy.

FIG. 1A illustrates a schematic of a system in accordance with a preferred embodiment of the present invention for optical power limiting applications using photo-induced anisotropy. A 532 nm output from a frequency doubled continuous wave (CW) or pulsed laser 12, for example, Nd:YAG laser is polarized by a polarizer $P_1$ 14, and divided into a reflected beam 38 (excitation beam) and a transmitted beam 36 (input beam) by a beam splitter 16. The excitation beam 38 is directed through a variable attenuator 30 and polarization rotator 32 to the thin film sample 22. The input beam 36 travels through a variable attenuator 18 and aperture 20 towards the film 22, and then an output beam 25 is directed to a detector 26 such as, for example, a laser power meter through a second polarizer $P_2$ 24. The polarizers $P_1$ and $P_2$ are crossed. The polarization of the excitation beam is fixed at an angle of 45±10 degrees to that of the input beam. In a preferred embodiment, the polarization of the excitation beam is fixed at an angle of 45 degrees to that of the input beam. Both beams overlap spatially on the same region on the sample, and the aperture ensures that the diameter of the input beam 36 is less than that of the excitation beam 38.

Figure 1B:
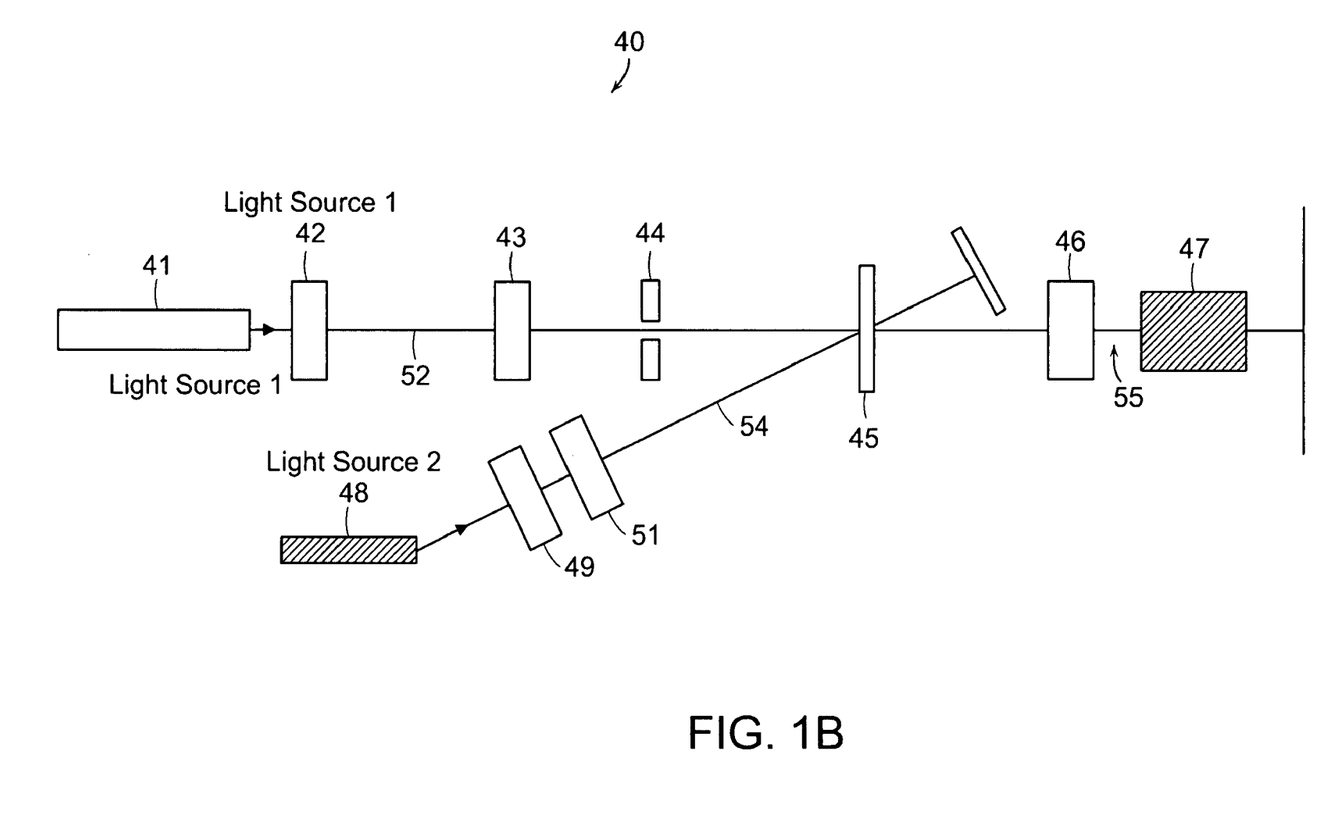
FIG. 1B illustrates a schematic of a system using two light sources in accordance with a preferred embodiment of the present invention.

FIG. 1B is a schematic diagram of a system having two light sources in accordance with a preferred embodiment of the present invention. An incoherent light source such as, for example, a light emitting diode 48 provides the excitation beam 54. The CW light source such as, for example, a laser 41 provides the input beam 52. The input beam is polarized by polarizer 42. The input beam travels through a variable attenuator 43 and aperture 44 towards the film 45 and then an output beam 55 is directed to a detector 47 such as, for example, a laser power meter or a sensor through a second polarizer 46. In a preferred embodiment, the second polarizer 46 is positioned to provide cross-polarization with respect to the polarizer 42. The excitation beam 54 is directed through a variable attenuator 49 and polarizer rotator 51 to the film sample 45 with 45 degree polarization. In a preferred embodiment, the excitation beam and the input beam can have the same wavelength or alternatively, preferred embodiments have different wavelengths for the input and excitation beam. The input wavelengths can range from wavelengths in the near infra-red spectrum to those in the visible region of the spectrum. The excitation beam can be blue or green or in between.

An azobenzene material of 4-dimethlyamino-azobenzene, is used in the systems in accordance with preferred embodiments of the present invention. The material has both optical properties of trans-cis photo-isomerization and photo-induced reorientation. The azobenzene molecules are embedded in the polymer matrix of polymethylmethacrylate (PMMA). To prepare the sample, initially azobenzene and PMMA are dissolved separately in chloroform at approximately 60° C. The solutions are then uniformly mixed by stirring them together for an hour, and are then coated onto an optical quality glass substrate. The thickness of the azobenzene-polymer film is approximately 50 μm, and the concentration of the azobenzene molecules in polymer is approximately 5% by weight. The film normally transmits 25% of the incident light at 532 nm. Alternate embodiments include films of different materials such as, for example, different azobenzene films, bacteriorhodopsin (BR) and films of materials having optical properties of trans-cis photo-isomerization, photo-induced reorientation and a high level of photo-anisotropy. Further, different polymers can be used for embedding the different photo-induced anisotropic materials. Embodiments include polymers such as, for example, polystyrenes and polycarbonates in the place of PMMA. In addition, the thickness of the film can vary in a range from micrometers to millimeters.

Figure 5:
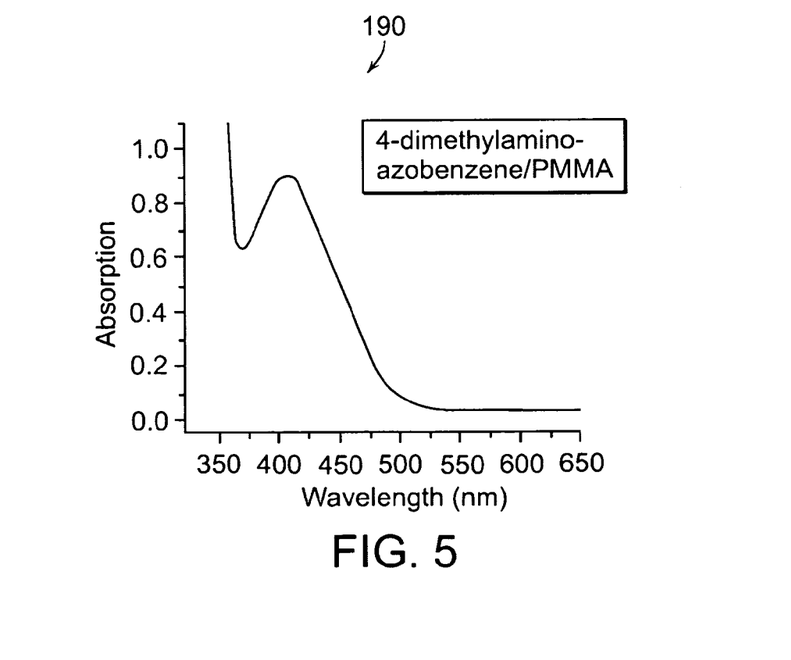
FIG. 5 illustrates the absorption spectrum of 4-dimethylamino-azobenzene PMMA film in accordance with a preferred embodiment of the present invention.

FIG. 5 shows the absorption spectrum of 4-dimethylamino-azobenzene PMMA film in accordance with a preferred embodiment of the present invention. It has a broad absorption band with a maximum absorption at 408 nm (full width at half-maximum (FWHM) is approximately 100 nm) because of the $\pi \rightarrow \pi^*$ and $n \rightarrow \pi^*$ transitions of the azobenzene molecules. The films also absorb light intensively in the UV region around 350 nm, which originates from the absorption of the PMMA polymer. Because of the overlap of absorption of its two isomers (trans and cis), the light-induced absorption change is small.

Figure 6:
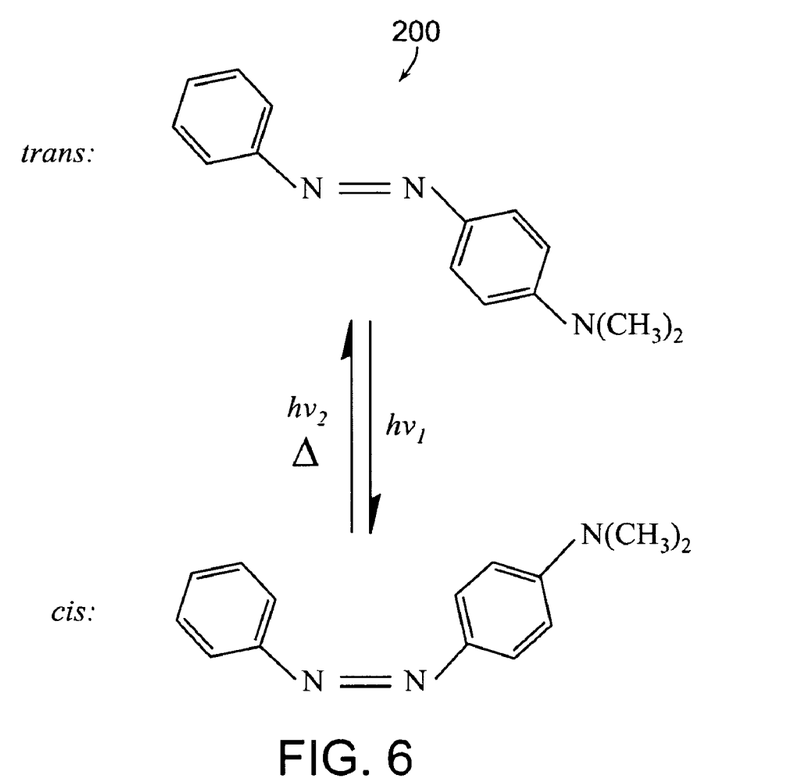
FIG. 6 illustrates the isomerization process of 4-dimethylamino-azobenzene in accordance with a preferred embodiment of the present invention.

Materials exhibiting photo-induced anisotropy have potential applications in information storage and information processing. It is well known that photo-induced molecular reorientation generally takes place in fluid systems such as liquid crystals. Nevertheless, by using polarized light it is possible to re-orient a random distribution of azobenzene molecules in solid matrices through a photo-induced trans-cis-trans isomerization process. The samples of PMMA polymer film doped with 4-dimethylamino-azobenzene in accordance with a preferred embodiment of the present invention present large photo-induced anisotropy. The molecule of 4-dimethylamino-azobenzene undergoes an isomerization process with excitation of light in the absorption band, as shown in FIG. 6.

In the absence of light, azobenzene exists in the trans form which is stable with an elongated structure, whereas, the photo-induced cis molecules have a bent shape and can revert to the trans form by thermal or photo-assisted isomerization with another wavelength. The length of the azobenzene segment in the trans form is approximately 1.0 nm whereas that of the cis form is only about 0.56 nm. This change of molecular dimension results in the bent cis form rotating more easily than the trans form. When the transition dipole moment of a molecule becomes perpendicular to the polarization of the excitation light its interaction with the light field ceases. Thus, after sufficient irradiation of an ensemble of chromophores, an enhancement of transition moments perpendicular to the polarization vector of the excitation light is achieved. It is this local ordering that leads to photo-induced anisotropy in the medium.

With an intensity increase of the input beam, the power limiting property is obtained by using the azobenzene film. FIGS. 2A–2D illustrate the results for optical power limiting for different intensity values in accordance with a preferred embodiment of the present invention. The dotted curves represent the linear transmission of the input beam in the absence of the excitation beam. In the presence of the excitation beam, the transmission of the input beam becomes nonlinear. With the increase of the input intensity, the results show a nearly perfect power limiting feature. In addition, the clamping threshold can be changed by choosing a different excitation intensity. For low intensities of the input beam, the presence of the excitation beam significantly enhances the output. At an intensity of 6.4 mW/cm$^2$ of the input beam, the measured transmission is 0.45% without the excitation beam, whereas it rises to 3% with an excitation intensity of 8 mW/cm$^2$ and to 11.6% with an excitation intensity of 91.6 mW/cm$^2$. Thus the linear transmission of the input beam can be enhanced by the excitation beam in this regime. On the other hand, for high intensities of the input beam, this enhanced output becomes limited and is finally clamped. For example, at the excitation intensity of 8 mW/cm$^2$, an increased intensity of 639 mW/cm$^2$ of the input beam results in a drastic drop of the transmission to 0.09%. Therefore, with the system in accordance with a preferred embodiment of the present invention, it is not only feasible to achieve the power-limiting feature but also easy to change the clamping threshold by choosing a different excitation intensity.

Figure 2A:
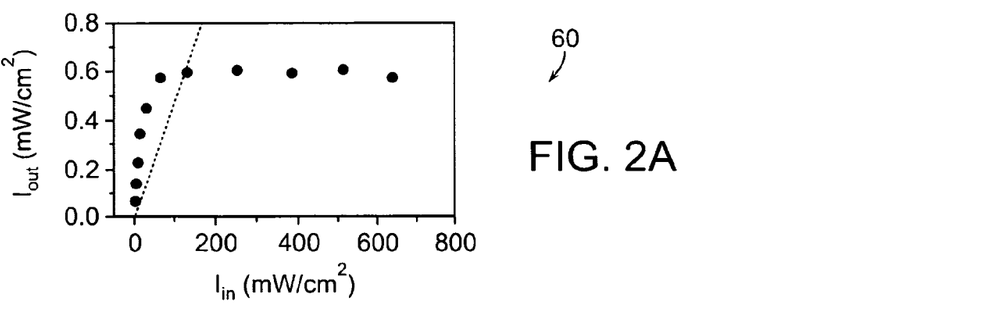
FIGS. 2A–2D graphically illustrate the optical power limitation provided by systems in accordance with a preferred embodiment of the present invention for different intensity values of the excitation beam specifically A) 8.0 mW/cm$^2$, B) 15.9 mW/cm$^2$, C) 424 mW/cm$^2$, and D) 91.6 mW/cm$^2$.
Figure 2B:
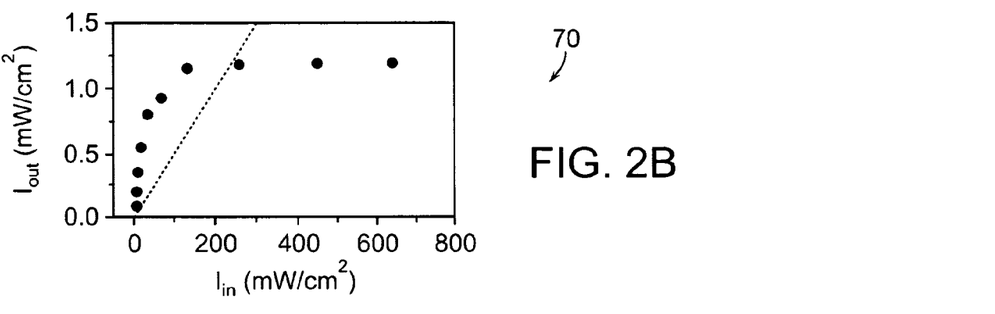
Figure 2C:
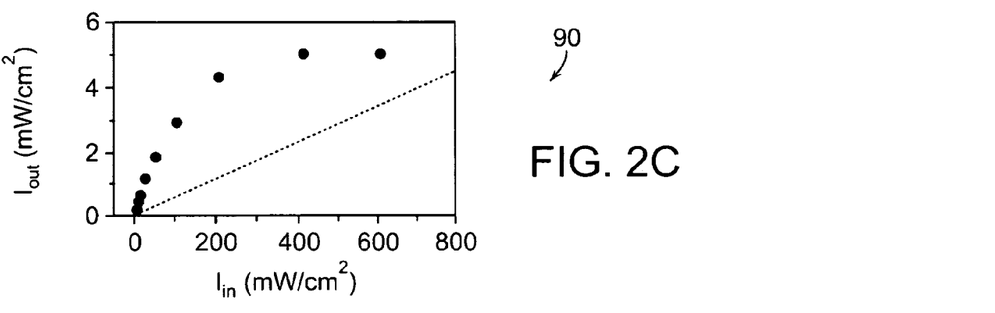
Figure 2D:
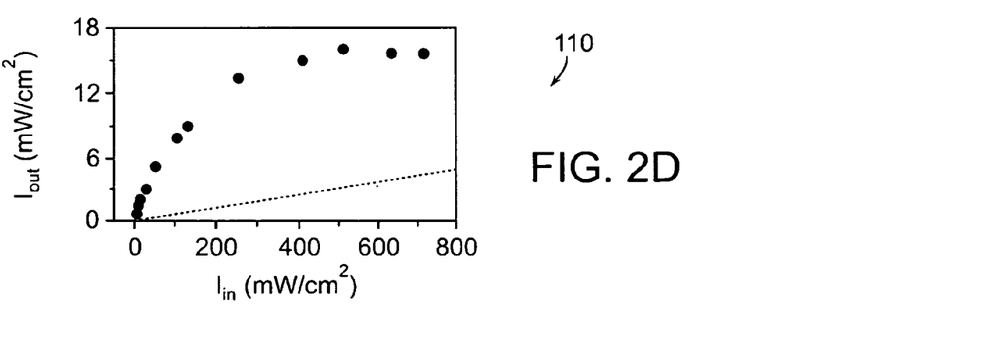
Figure 2E:
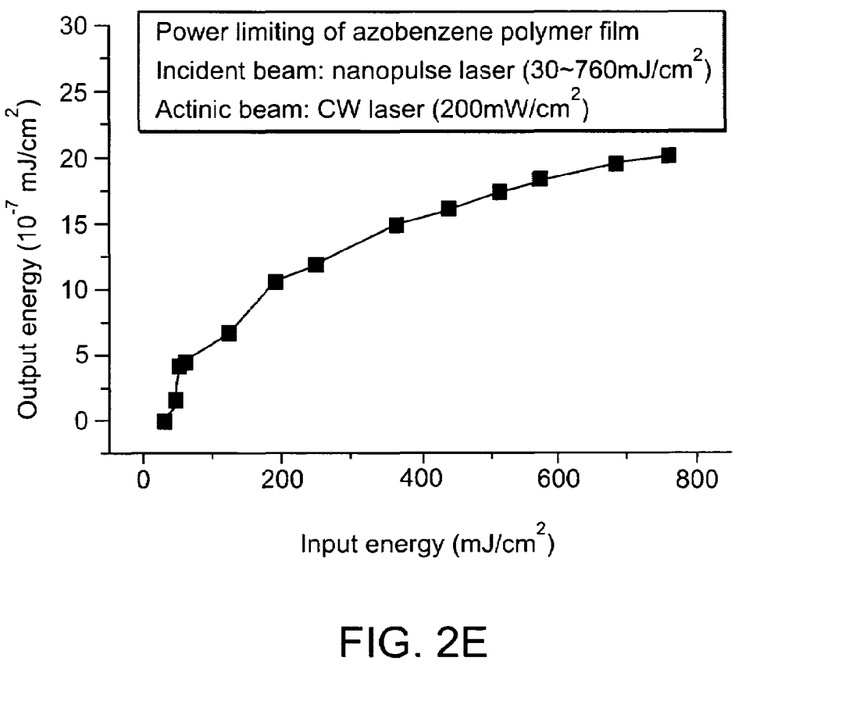
FIG. 2E graphically illustrates the power limiting of an azobenzene polymer film in which the incident beam is a nanopulsed laser.

FIG. 2E illustrates the power limiting characteristics of an azobenzene polymer film in which the incident beam is a nanopulse laser. The energy of the incident beam is in the range of 30–760 mJ/cm$^2$. The laser can be a 5 ns frequency—doubled Nd:YAG pulsed laser or a picosecond pulsed laser, for example.

Figure 3A:
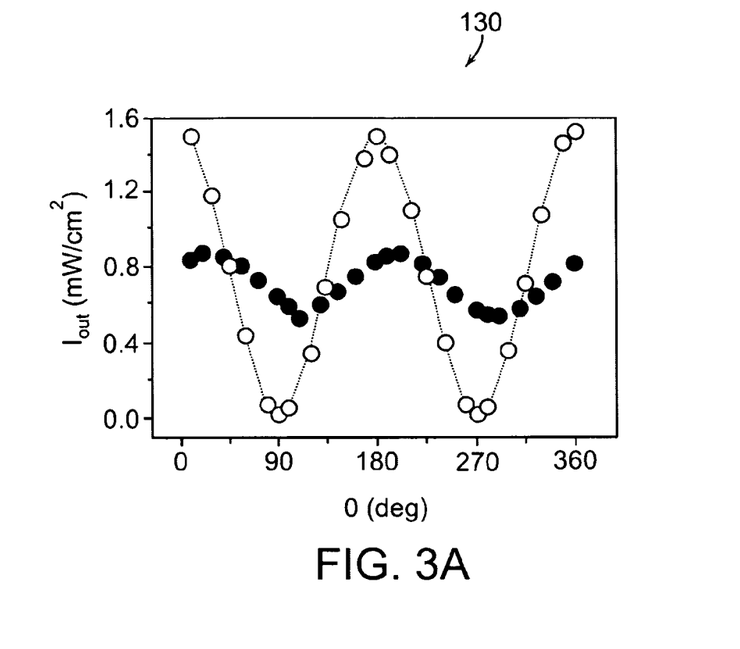
FIGS. 3A and 3B illustrate the graphs of photo-induced anisotropy in the azobenzene film in accordance with a preferred embodiment of the present invention in both Cartesian and polar coordinates, respectively.
Figure 3B:
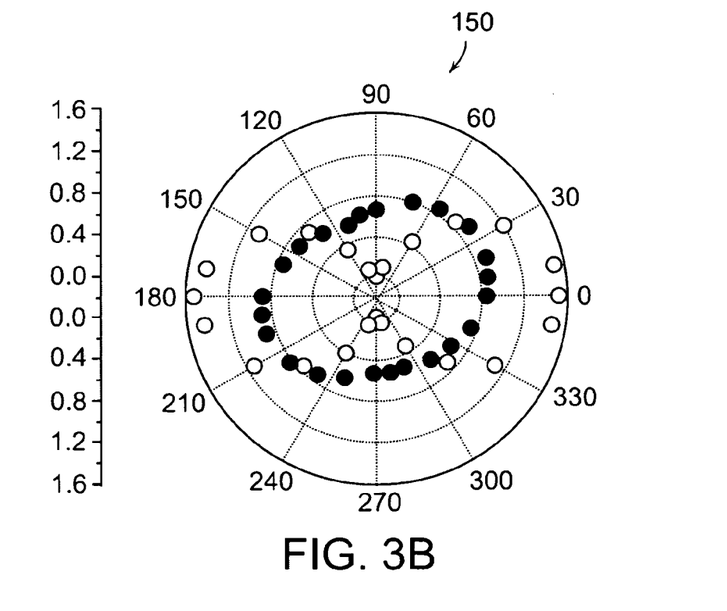

The mechanism of power limiting properties can be understood with the photo-induced anisotropy of the azobenzene film. The photo-induced anisotropy including both photo-induced birefringence and photo-induced dichroism are intensity-dependent in azobenzene film which results in the possibility of controlling output intensity with the input intensity. To analyze the property of photo-anisotropy, the transmission of the input beam was measured for different angular orientation $\theta$ of the analyzer $P_2$ 24 ($\theta=0$ being parallel to the polarization direction of polarizer $P_1$ 14). The results are shown in FIGS. 3A and 3B which illustrate graphically photo-induced anisotropy in the azobenzene film both in Cartesian and polar co-ordinates, respectively. In the absence of the excitation beam, the angular intensity distribution of the transmitted input beam fits closely to a $\cos^2 \theta$ function, whereas in the presence of excitation beam the output is transformed to elliptical polarization. This happens because of the photo-anisotropic effect of the azobenzene film induced by the linearly polarized excitation beam. The transition moment of the azobenzene molecule lies along the molecular axis, and only these molecules with their axis orientation parallel to the electric vector absorb light and are then isomerized from trans form to cis form. The cis form is unstable and will go back to trans form which may be isomerized to cis form again if its transition moment is not perpendicular to the electrical direction of the light field. The repeated trans-cis-trans isomerization results in the alignment of azobenzene molecules in the direction perpendicular to the polarization of the excitation beam. This molecular alignment causes the photo-induced birefringence that makes the output polarization elliptical and the photo-induced dichroism that makes the semi-major axis of the ellipse shift through a rotation angle from the $\theta=0$ plane. Both mechanisms contribute to the optical power-limiting property. However, for the azobenzene film, the photo-induced birefringence will dominate as compared with the photo-induced dichroism.

The semi-minor axes of the ellipse depend on the relative values of the input and excitation intensities. The photo-induced polarization ellipse originates from a phase retardation $\Gamma$, which is given by $\Gamma = \Delta n \pi d/\lambda$ where $d$ is the film thickness and $\lambda$ is the input wavelength. $\Delta n = n_\perp - n_\parallel$ is the birefringence where $n_\perp$ and $n_\parallel$ are the respective components of the index of refraction perpendicular and parallel to the excitation beam polarization. Estimates of the phase retardation $\Gamma$ can be obtained from the transmission equation $I = I_0 \sin^2 \Gamma$, where $I_0$ is the input intensity before $P_2$ and $I$ is the intensity after $P_2$.

Figure 4:
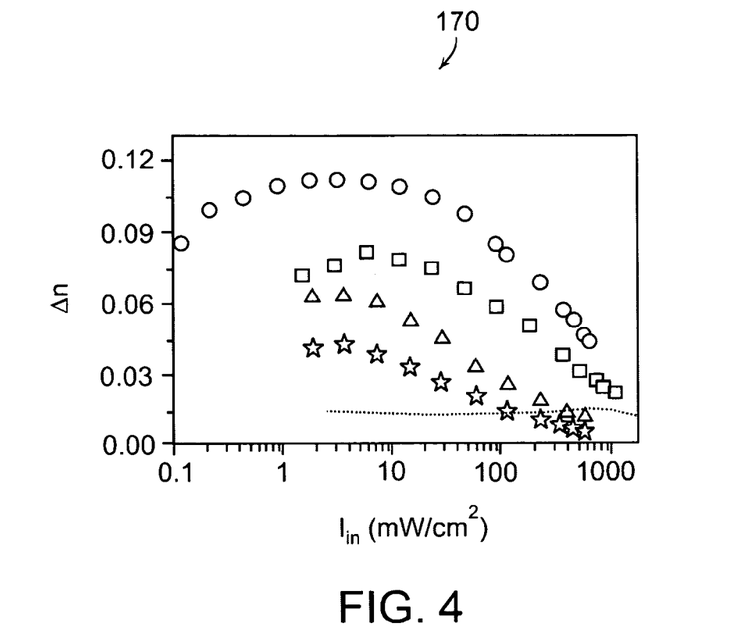
FIG. 4 graphically illustrates the variation of Δn with the intensity of the input beam in accordance with a preferred embodiment of the present invention.

FIG. 4 illustrates the results of birefringence $\Delta n$ as a function of input intensity. When the excitation beam is absent, $\Delta n$ is close to zero. In the presence of the excitation beam, $\Delta n$ is higher and shows an initial increase with input intensity, which is however followed by a decrease towards zero at higher input intensities. For a device in accordance with a preferred embodiment of the present invention, this characteristic is more desirable since it ensures enhanced transmission at low intensities and limited transmission at high intensities. The observed limiting of power can be explained on the basis of the results of intensity-dependent photo-induced anisotropy of the azobenzene film. In the region of weak intensity of the input beam, the photo-induced anisotropy is relatively large and changes the polarization of input beam which leads to an enhanced transmission through the crossed polarizers. On the other hand, with a relatively strong intensity of input beam the photo-anisotropic effect is reduced, so that the input beam gets blocked by the crossed polarizer $P_2$. In addition, the photo-induced anisotropy also depends on the intensity of excitation beam. With higher excitation intensity, the photo-induced birefringence of azobenzene film is shifted to the region of larger values. Therefore, by choosing the values of excitation intensity the clamping threshold of power limiting can be controlled.

The optical processes such as nonlinear absorption, nonlinear scattering, and beam diffusing have been extensively investigated for limiting power with various materials, and there is recent interest in nanoscopic materials as well. However, none of them provide smooth and complete clamping of the output as observed in the embodiments of the present invention. In addition, the use of crossed polarizers in preferred embodiments results in a normally opaque (NO) optical limiter, in the sense that it is essentially an opaque device in which a transparency at low inputs is induced by photo-induced anisotropy. Conventional optical limiters are normally transparent (NT) devices in comparison, in which an opacity at high inputs is induced by nonlinear optical phenomena. In general, a NO device offers an unmistakable advantage in terms of detector safety. To appreciate this advantage using a preferred embodiment, two worst-case situations can be made safe wherein either the excitation beam becomes accidentally blocked or the film becomes transparent by photodamage. In both cases the output remains within safe limits by virtue of the presence of the crossed polarizers. On the other hand an NT device with parallel polarizers can severely imperil detector safety under such circumstances.

The transition time from the NT-to-NO state is found to be a few seconds with high intensity of input and excitation beams because of the photo-induced anisotropic effect of azobenzene films. With lower intensity, the NT-to-NO transition time become relatively slow (tens of seconds). In the absence of an excitation beam, the films are not transparent as the polarization of input light is not rotated and blocked by the polarizer behind the sample. The response time of observed induced anisotropy is in agreement with earlier reports of the time evolution of photo-induced birefringence observed in side-chain polymers containing aminonitro azobenzene. However, there are environments in which photo-induced reorientation is much faster. For example, in Langmuir-Blodgett films of side-chain polymers containing some derived aminoazobenzene chromophores, the anisotropy buildup time is less than 20 ns. It is suggested that the primary driving mechanism for induced anisotropy in these films is not trans-cis-trans isomerization, but a vibronic dissipation of the electronic excitation energy that increases the rotational mobility of the chromophores collectively. Methods are also available to enhance the birefringence, and hence the low-intensity transmission through the film if required. One method to enhance the birefringence includes shining red light on the sample to photo assist the cis-trans isomerization. In preferred embodiments, birefringence can also be promoted by a controlled heating of the sample to certain optimal temperatures below the glass transition temperature. Similarly, choosing a higher visible wavelength for the input beam can result in a corresponding higher photo-induced anisotropy, in addition to a lower absorption in the film. Apart from the protection of sensitive detectors, one practical application of a device in accordance with a preferred embodiment of the present invention is a user-friendly laser goggle for protection against low-power CW or pulsed lasers. According to the American National Standard for Safe Use of Lasers (ANSI Z136.1, 2000), a visible laser (400–700 nm) operating at less than a 1-mW power is considered safe for an exposure time of 0.25 s or less. Unfortunately, however, even some laser pointers can emit 5 mW of power that can be hazardous if viewed even for a short time. Therefore laser eye protection even at a low-power region is extremely important.

Figure 7:
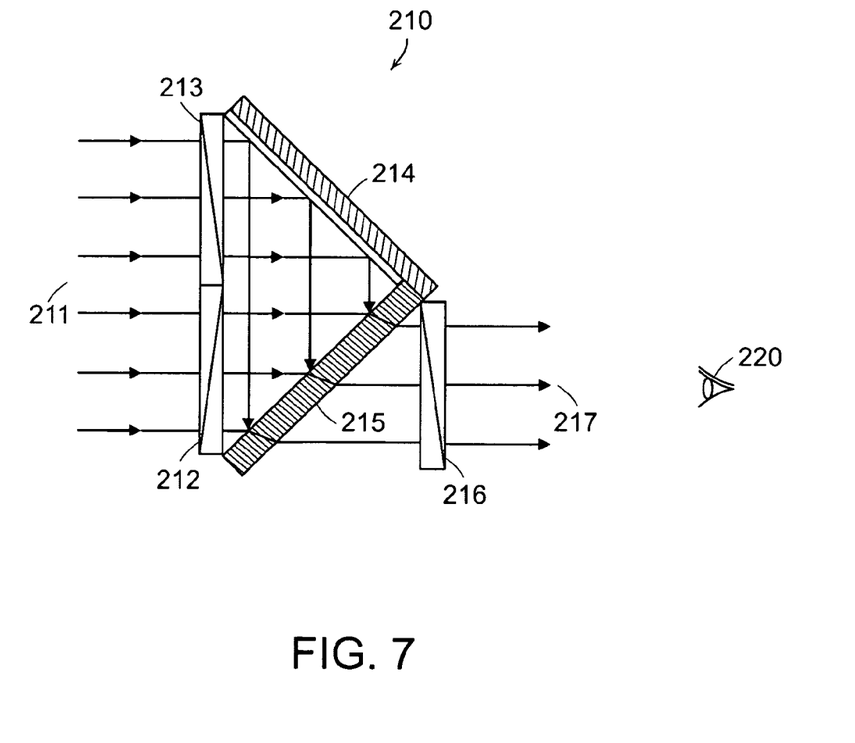
FIG. 7 is a schematic diagram of a device in accordance with a preferred embodiment of the present invention having one light source.

FIG. 7 illustrates a schematic diagram of a device in accordance with a preferred embodiment of the present invention having one light source. The input beam 211 is provided by a CW or pulsed light source and a first portion of the input beam travels through the vertical polarizer 212 while a second portion travels through another polarizer 213 fixed at an angle of 45 degrees to that of the input beam and forms the excitation beam. The excitation beam then travels to a reflective element, for example, mirror 214 and then to the film sample 215. The input beam travels to the film sample 215, and then to the detector or eye 220 through a second polarizer 216 which is a horizontal polarizer. The output beam 217 is sensed at a detector system or by a human. This embodiment can be used for laser eye protection such as an eye-goggle made from a polymer such as, for example, a polycarbonate, embedded with a photo-induced anisotropic material like azobenzene to form the film. Laser eye protection for both low (mW range) and high power applications, using CW or pulsed lasers, respectively, can benefit from preferred embodiments of the present invention. In an embodiment, laser eye protection in a low power region can be useful as even in the low power region a laser pointer with 1 mW power can be hazardous for eyes if viewed for more than 0.25 seconds. The embodiments of the present invention provide laser light at safe levels allowing for laser alignment and other uses.

Figure 8:
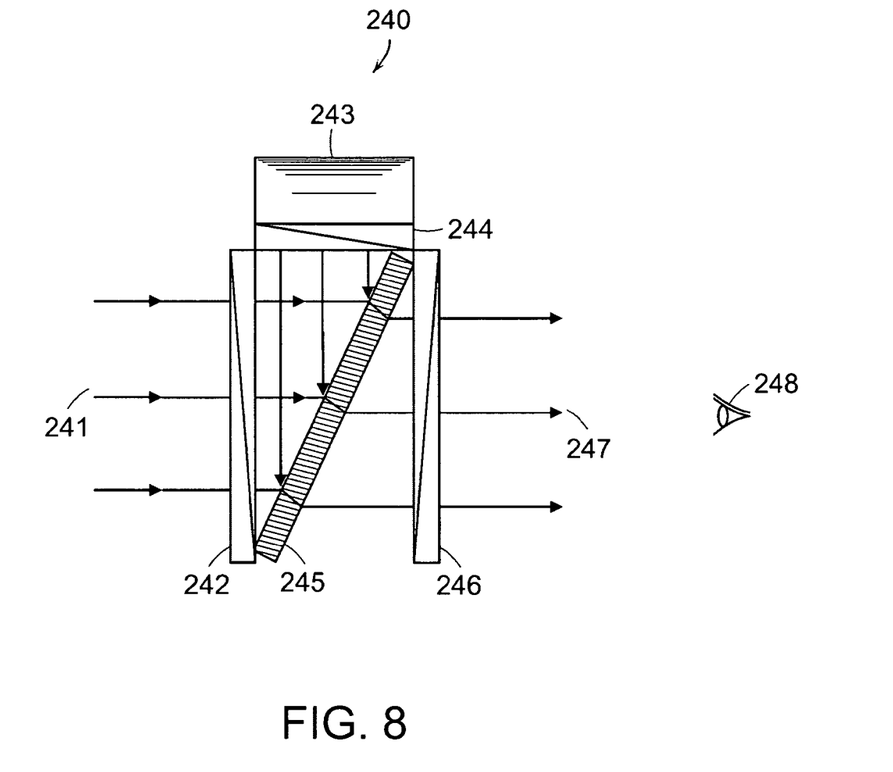
FIG. 8 is a schematic diagram of a device in accordance with a preferred embodiment of the present invention having two light sources.

FIG. 8 is a schematic diagram of a device in accordance with a preferred embodiment of the present invention having two light sources. The device operates similar to the device described with respect to FIG. 7 but has an additional light source to provide the excitation beam. In this preferred embodiment, the second incoherent light source is an illuminating laser diode 243. Alternate embodiments can include other incoherent light sources such as, for example, but not limited to, light emitting diodes. The input beam 241 travels through the vertical polarizer 242 to the sample film 245 and then further to the detector 248 after traveling through a horizontal polarizer 246. The excitation beam generated by the laser diode 243 travels to a polarizer positioned at an angle of approximately 45 degrees to that of the input beam and then to the sample 245.

Preferred embodiments of the present invention provide an ideal optical limiter that can be made by placing a photo-anisotropic material between crossed polarizers. The photo-induced anisotropy leads to an enhanced transmission of the input beam at low input intensities and output clamping at high input intensities. The limiting threshold is adjustable. Crossed polarizers ensure absolute safety of the detector in the event of any malfunction in the system. Since the limiting mechanism is quite general, the device can be operated at different wavelengths with suitable materials such as from near infra-red wavelengths to wavelengths in the visible range. In addition, the azobenzene materials are found to be stable when exposed to continuous wave (CW) as well as pulsed lasers. Preferred embodiments can be useful to limit high-energy fast laser pulses.

In addition to power limiting applications, a preferred embodiment of the present invention can be used in medical image processing using the same principle of photo-induced anisotropic effect with Bacteriorhodopsin (BR) films.

The claims should not be read as limited to the described order or elements unless stated to that effect. Therefore, all

What is claimed:

1. A system for limiting power, comprising:
   a light source to provide an input light beam along a first optical path;
   a first polarizing element having a first polarization state positioned in the first optical path;
   a second polarizing element positioned in the first optical path having a second polarization state relative to the first polarization state;
   a sample having a photo-induced anisotropic material positioned in the first optical path; and
   a polarizer positioned in a second optical path at an angle to that of the input beam such that an excitation beam provided in the second optical path spatially overlaps the input beam on the sample, and an output beam that is generated having a reduced transmission value.

2. The system of claim 1, wherein the light source is a continuous wave laser.

3. The system of claim 1, wherein the sample comprises an azobenzene material embedded in a polymer.

4. The system of claim 3, wherein the polymer is one of polystyrene, polycarbonate and a matrix of polymethylmethacrylate.

5. The system of claim 1, wherein the sample is integral with an eye protection goggle.

6. The system of claim 1, wherein the wavelength of the input beam is in a range between near infra-red radiation and a visible spectrum.

7. The system of claim 1, further comprising a detector system.

8. The system of claim 7, wherein the detector system is a power meter.

9. The system of claim 1, further comprising an incoherent light source to generate the excitation beam.

10. The system of claim 9, wherein the incoherent light source is one of a laser diode or light emitting diode.

11. The system of claim 1 wherein the light source is a pulsed laser.

12. The system of claim 1 wherein the angle of second optical path is in a range of 35–55 degrees relative to the first optical path of the input beam.

13. An optical power limiter, comprising:
    a light source to provide an input light beam along a first optical path;
    a first polarizing element having a first polarization state positioned in the first optical path;
    a second polarizing element positioned in the first optical path having a second polarization state substantially orthogonal to the first polarization state;
    a sample having a photo-induced anisotropic material positioned in the first optical path; and
    a polarizer positioned in a second optical path at an angle in the range of 35–55 degrees to that of the input beam such that an excitation beam provided in the second optical path spatially overlaps the input beam on the sample, and an output beam that is generated has a reduced transmission value.

14. A method of limiting optical power, comprising the steps of:
    generating an input beam from a first light source;
    generating a linearly polarized excitation beam;
    exposing a sample having a photo-induced anisotropic material to the input beam and the excitation beam; and
    cross-polarizing the input beam.

15. The method of claim 14 further comprising clamping the transmission of the output beam.

16. The method of claim 14 further comprising using a pulsed laser to generate the input beam.

17. The method of claim 14 further comprising providing a material including an azobenzene material in a polymer.

18. An eye protection device, comprising:
    a light source to provide an input light beam along a first optical path;
    a first polarizing element having a first polarization state positioned in the first optical path;
    a second polarizing element positioned in the first optical path having a second polarization state substantially orthogonal to the first polarization state;
    a sample having a photo-induced anisotropic material positioned in the first optical path; and
    a polarizer positioned in a second optical path at an angle in a range of 35–55 degrees to that of the input beam such that an excitation beam provided in the second optical path spatially overlaps the input beam on the sample, and an output beam that is generated has a reduced transmission value.

19. The device of claim 18 wherein the excitation beam has an intensity of at least 8 mW/cm$^2$.

20. The device of claim 18 wherein an output polarization is elliptical.

* * * * *